US012791506B2

(12) United States Patent
Bosch Ros et al.

(10) Patent No.: US 12,791,506 B2
(45) Date of Patent: Nov. 10, 2026

(54) SYSTEM AND METHOD FOR THE EVALUATION OF THE HYDRIC STATE OF A PLANT

(71) Applicant: HYDROSTAT CEN, SL, Santa Maria Iles Balears (ES)

(72) Inventors: David Bosch Ros, Sabadell (ES); Álvaro Sanz Gómez, Palma de Mallorca (ES); Ignacio Tortosa Montojo, Palma de Mallorca (ES); Antoni Palerm Llabrés, Son Servera (ES); José Mª Martí Sauras, Binissalem (ES); José Mariano Escalona Lorenzo, Palma de Mallorca (ES); Hipólito Medrano Gil, Palma de Mallorca (ES)

(73) Assignee: HYDROSTAT CEN, SL, Santa Maria Iles Balears (ES)

( * ) Notice: Subject to any disclaimer, the term of this patent is extended or adjusted under 35 U.S.C. 154(b) by 136 days.

(21) Appl. No.: 18/861,345

(22) PCT Filed: May 3, 2023

(86) PCT No.: PCT/EP2023/061636
§ 371 (c)(1),
(2) Date: Oct. 29, 2024

(87) PCT Pub. No.: WO2023/213861
PCT Pub. Date: Nov. 9, 2023

(65) Prior Publication Data

US 2025/0290884 A1 Sep. 18, 2025

(30) Foreign Application Priority Data

May 6, 2022 (EP) .................................... 22382436

(51) Int. Cl.
*G01N 27/04* (2006.01)
*G01N 33/00* (2006.01)

(52) U.S. Cl.
CPC ....... *G01N 27/048* (2013.01); *G01N 33/0098* (2013.01)

(58) Field of Classification Search
None
See application file for complete search history.

(56) References Cited

U.S. PATENT DOCUMENTS 9,857,391 B2 1/2018 Shimokawa et al.
2024/0402144 A1* 12/2024 Bloomer ............ G01N 33/0098

FOREIGN PATENT DOCUMENTS

CN 111189885 A 5/2020
CN 113418963 A 9/2021
(Continued)

OTHER PUBLICATIONS

International Search Report and Written Opinion for Corresponding International Application No. PCT/EP2023/061636, Jul. 27, 2023, 9 pages.

*Primary Examiner* — Jas A Sanghera
(74) *Attorney, Agent, or Firm* — LUCAS & MERCANTI, LLP

(57) ABSTRACT

A system and method for the evaluation of the hydric state of a plant is proposed. The system comprises: two electrodes separated a certain distance, and adapted for insertion, in the trunk of a plant to establish galvanic contact; a temperature sensor; an electronic unit including a voltage measurement module configured to apply, during a first interval, an electrical voltage, with a given polarity, on the electrodes; to invert, sequentially, during a second interval, the given polarity; and to measure, simultaneously, the temperature of the electrodes and the voltage resulting from the application of electrical voltage in both polarities. A processing unit
(Continued)

calculates an electrical conductance value from the applied electrical voltage and the resulting measured voltage and infers the hydric state of the plant from the calculated conductance value and the measured electrode temperature.

15 Claims, 2 Drawing Sheets

(56) References Cited

FOREIGN PATENT DOCUMENTS

| | | | |
|---|---|---|---|
| CN | 114020065 | A | 2/2022 |
| DE | 102006026557 | A1 | 12/2007 |
| EP | 3104135 | A1 | 12/2016 |
| JP | H06273434 | A | 9/1994 |
| KR | 101996404 | B1 | 7/2019 |
| WO | 2007039537 | A1 | 4/2007 |
| WO | 2022039007 | A1 | 2/2022 |

* cited by examiner

SYSTEM AND METHOD FOR THE EVALUATION OF THE HYDRIC STATE OF A PLANT

CROSS REFERENCE TO RELATED APPLICATIONS

This Application is a 371 of PCT/EP2023/061636 filed on May 3, 2023, which claims priority of European Patent Application No. 22382436.8 filed May 6, 2022, the contents of each of which are incorporated herein by reference.

TECHNICAL FIELD

The present invention concerns a system, sometimes implemented as a device, and a method, for the evaluation of the hydric state of a plant, in the stem, branch or trunk.

BACKGROUND OF THE INVENTION

U.S. Pat. No. 9,857,391B2 discloses a plant water dynamics sensor comprising a heater-equipped temperature probe including a temperature sensor and a heater; a temperature probe including a temperature sensor; an electrical resistance probe including an electrical resistance measurement electrode; and a support that supports the probes while the probes are aligned parallel to each other. The position of a xylem XY can be detected based on an electrical resistance measured at the electrical resistance probe, so that each of the temperature sensors can be arranged correctly in a position at a phloem PH or at the xylem XY. This facilitates attachment of a plant water dynamics sensor and water dynamics in a plant can be measured with high accuracy.

JPH06273434 discloses a measuring apparatus of the flow velocity of water content mainly inside the trachea of a plant. The measuring apparatus is composed of a measurement part in which a heater protruding from a mounting seat is installed, in which a first temperature sensor and a second temperature sensor are installed so as to protrude from the mounting seat toward the same direction as the heater and so as to sandwich the heater, and in which a third temperature sensor is installed between the first temperature sensor and the heater. The measuring apparatus is composed of a computer with a built-in program which measures the temperature difference between the first temperature sensor and the second temperature sensor and the temperature difference between the first temperature sensor and the third temperature sensor by the measurement part and which computes a flow velocity by a computation formula stored in advance by transmitting the product of both temperature differences.

KR101996404B1 relates to a portable type and installation type tree management device capable of managing trees by species scientifically and systematically. The device comprises a first measuring unit including a pair of electrodes each having a plurality of needles for insertion into a tree trunk, and measuring electrical conductivity; a diagnosis unit diagnosing the health state of a tree based on the measured electrical conductivity; and a communication unit transmitting the diagnosed health state of the tree to the user.

CN111189885A relates to a trunk moisture content measuring method based on equivalent power supply internal resistance. The method comprises selecting two points on a trunk along the axial direction and respectively arranging a metal electrode a and a metal electrode b; calculating the internal resistance of a power supply formed by the metal electrode a, the metal electrode b and the trunk; and calculating the trunk moisture content through a relation model MC=f (Ri) between the trunk moisture content and the power supply internal resistance.

CN113418963A discloses a trunk freeze-thaw impedance image real-time detection method and system. The method comprises the steps: constructing a multi-frequency sweep frequency method based on the impedance characteristics of a trunk, manufacturing a measurement probe comprising a plurality of conical stainless steel electrodes, and building a two-end hybrid drive excitation method based on the measurement probe, and used for acquiring trunk cross section freeze-thaw impedance characteristic information data; performing regularization processing and two-dimensional image reconstruction and correction to obtain a trunk freeze-thaw impedance two-dimensional image; performing correction to obtain a trunk freeze-thaw impedance diagram; and establishing a trunk freeze-thaw information real-time sensing model based on the freeze-thaw impedance image, and calculating the real-time freeze-thaw degree and freeze-thaw depth of the trunk in the wintering period. The system comprises a trunk cross section freeze-thaw impedance acquisition unit, a trunk freeze-thaw impedance two-dimensional image reconstruction unit, a temperature compensation unit and a trunk freeze-thaw information real-time sensing unit.

Despite the known solutions for the evaluation of the hydric state of a plant, i.e. the amount of water the plant has, there is still a need for alternative, faster, more reliable and accurate systems and methods.

DESCRIPTION OF THE INVENTION

To that end the present invention proposes, according to a first aspect, a system for evaluating the hydric state of a plant. The system comprises at least two electrodes spaced a certain distance apart, and adapted for its insertion, at a given depth, into the trunk of a plant to establish galvanic contact with the plant; at least one temperature sensor of the electrodes; an electronic unit, operatively connected to the two electrodes and the temperature sensor of the electrodes; and a processing unit, having a memory and one or more processors.

According to the present invention, the electronic unit includes a voltage measurement module which is responsible for: applying, during a determined first time interval, an electric voltage, with a determined polarity, on the electrodes; inverting, in a sequential manner, during a determined second time interval, said determined polarity; and measuring voltage values resulting from said application of electric voltage in both polarities carried out during said first and second time intervals. The temperature sensor of the electrodes, at the same time as said measurement, measures the temperature of the electrodes. Finally, the processing unit, by means of one of its processors, calculates the electrical conductance value from the applied electrical voltage and the resulting measured voltage values, and infers a value relative to the hydric state of the plant by processing the calculated conductance value and the measured electrode temperature.

Embodiments of the present invention also provide, according to a second aspect, a method for assessing the hydric state of a plant. The method comprises: inserting, at a given depth, at least two electrodes in the trunk of a plant, wherein the two electrodes maintain galvanic contact with the plant and are separated a certain distance from each other; inserting a temperature sensor of the electrodes; applying, by an electronic unit, during a first time interval and with a given polarity, an electric voltage on the electrodes; reversing, by the electronic unit, sequentially, during a second time interval, said given polarity; to measure, by the electronic unit using, simultaneously, a voltage measurement module and said electrode temperature sensor, voltage values resulting from the application of electric voltage in both polarities carried out during said first and second time intervals, and the temperature of the electrodes; calculating, by a processing unit, an electrical conductance value from the applied electrical voltage and the resulting measured voltage values; and inferring, by the processing unit, a value relating to the hydric state of the plant by processing the calculated conductance value and the measured electrode temperature.

In some embodiments, the voltage measurement module comprises a Wheatstone bridge that allows the passage of electric current resulting from the electric voltage applied across it.

In some embodiments, the system/device further comprises an analog-to-digital converter for, prior to processing, converting said resulting voltage values and the measured electrode temperature into equivalent digital signals.

In some embodiments, the electronic unit further comprises an electrical power supply (e.g., one or more batteries, photovoltaic panels, or thermoelectric generators).

In some embodiments, an ambient temperature sensor is also included. Likewise, the system/device can also include an ambient humidity sensor, a light radiation sensor, a geopositioning system, an internal operational error checking system and/or a real-time clock.

In some embodiments, a system for attaching the electronic unit to the trunk of the plant is also included. Further, the electronic unit can contain a visualization interface, e.g., a screen, or alternatively or complementarily, a voice interface.

In an embodiment, the processing unit is remote to the electronic unit. In this case, both elements include a communications module, wireless or wired, and the electronic unit can also include a local processing unit. Alternatively, the processing unit is included in (i.e., local to) the electronic unit. In this case, the electronic unit comprises a communications module, wireless or wired.

In some embodiments, simultaneous to the measurement step, a measurement of an ambient temperature near the plant is also performed. Likewise, in some examples, a measurement of other parameters, such as ambient humidity, light radiation, geolocation and/or a time stamp, can also be performed.

In some embodiments, the first time interval and the second time interval have a fixed duration. In other embodiments, the application and inversion are performed until a stabilization of the electrical voltage in an area where the two electrodes are inserted.

BRIEF DESCRIPTION OF THE DRAWINGS

The previous and other advantages and features will be more fully understood from the following detailed description of embodiments, with reference to the attached figures, which must be considered in an illustrative and non-limiting manner, in which.

DETAILED DESCRIPTION OF THE INVENTION AND OF SOME EMBODIMENTS

The present invention provides a system (sometimes implemented as a device or apparatus) and a method for the evaluation of the hydric state of a plant.

Said hydric state can be objectively defined from physiological variables measured in the plant. The most widely used in the field of plant physiology and agronomy is the hydric potential. This is defined as the capacity of water molecules to move freely through a given medium. In the case of plants, it refers to the capacity to transport or mobilize water through the cellular tissue of the plant, a function and condition necessary to stay alive.

In the case of the proposal presented here, hydric potential refers to the plant's branch hydric potential. The measurement of hydric potential is carried out by applying pressure to extract water from the plant through the leaf, specifically through the petiole of a leaf. For this purpose, use is generally made of a pressure pump or Scholander chamber.

More particularly, in the present case, methodologically, the measurement is made to be representative of the branch hydric potential, causing the closure of the stomata of the leaf to be measured so that its hydric potential is equalized with that of the branch on which it is located.

Therefore, the proposal presented is related to a system and a method for the measurement of the hydric potential as a representative indicator of the hydric state of a plant.

Figure 1:
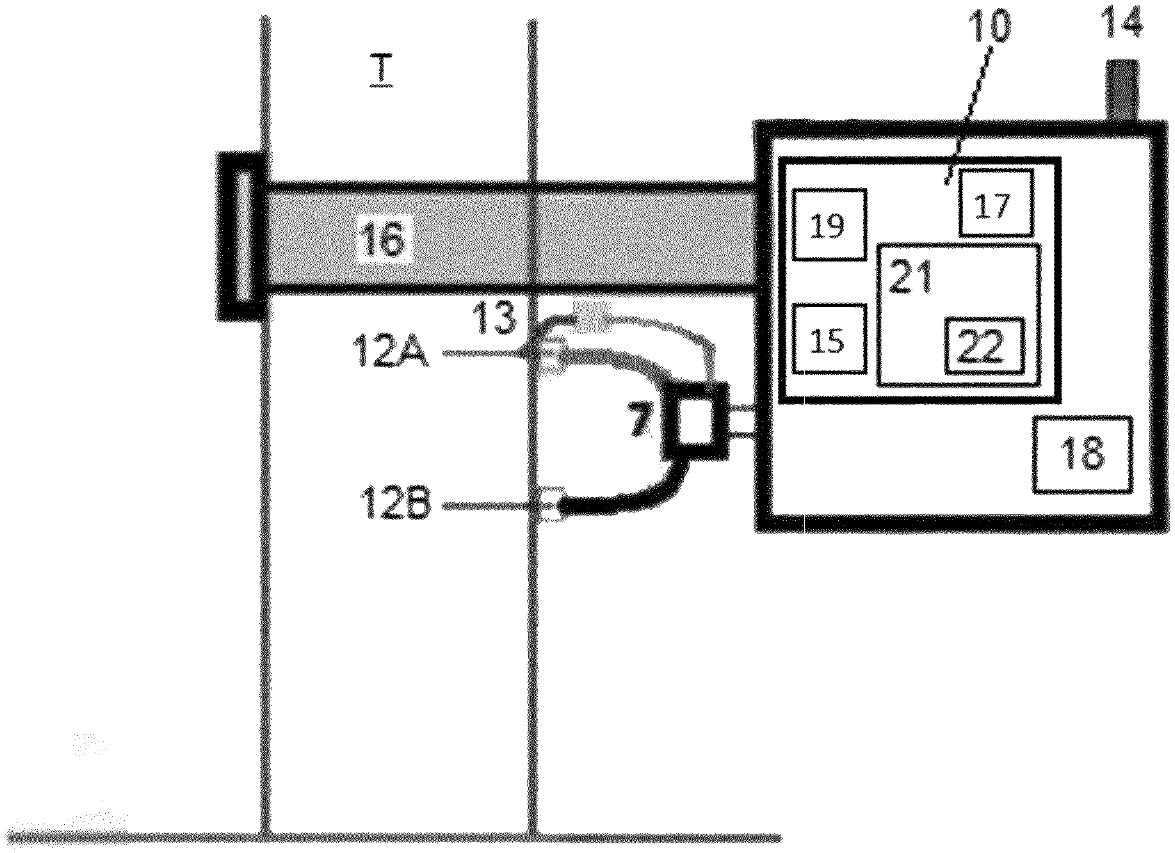
FIG. 1 schematically illustrates an embodiment of the proposed system for measuring the hydric state of a plant.

With reference now to FIG. 1, therein an embodiment of the proposed measuring system/device is illustrated. According to this particular example, the measuring system comprises an electronic unit (10), two electrodes (12A) and (12B), a temperature sensor of the electrodes (13), an ambient temperature sensor (14), and an electrical power supply (18). The measuring system is attached to the trunk (T) of the plant by means of a fastening system (16), e.g., straps, or the like.

As shown in the figure, the two electrodes (12A, 12B) are spaced a certain distance apart and connected to the temperature sensor (13) by means of a connection element (7).

The electronic unit (10), according to this particular example, includes a voltage measurement module (21), a processing unit (17), a communications unit (19), preferably wireless, and an analog/digital converter (15) for digitalization of the data/parameters obtained with the rest of the elements/sensors. The voltage module (21), as also illustrated in FIG. 1, comprises a Wheatstone bridge (22). Not limiting, since in other alternative embodiments other alternative electronic resistance measurement circuits can be used.

In addition to the aforementioned processing unit (17), a second processing unit external or remote to the measuring system/device can be included. In this case, the processing unit (17) local to the electronic unit (10) would not perform any data processing, but would only communicate the measured data/parameters to the external or remote processing unit for processing.

Although not illustrated in FIG. 1, for simplicity thereof, the proposed measurement system can include additional elements/sensors, such as, an environmental humidity sensor, a light radiation sensor, a geopositioning system, an internal operating error checking system, a real-time clock, etc.

In other embodiments, in this case not illustrated, the measurement system may not contain the ambient temperature sensor (14) or the analog/digital converter (15). Also, the electronic unit (10) may not include any processing unit with all calculations/processing being performed remotely to the measurement device.

Figure 2:
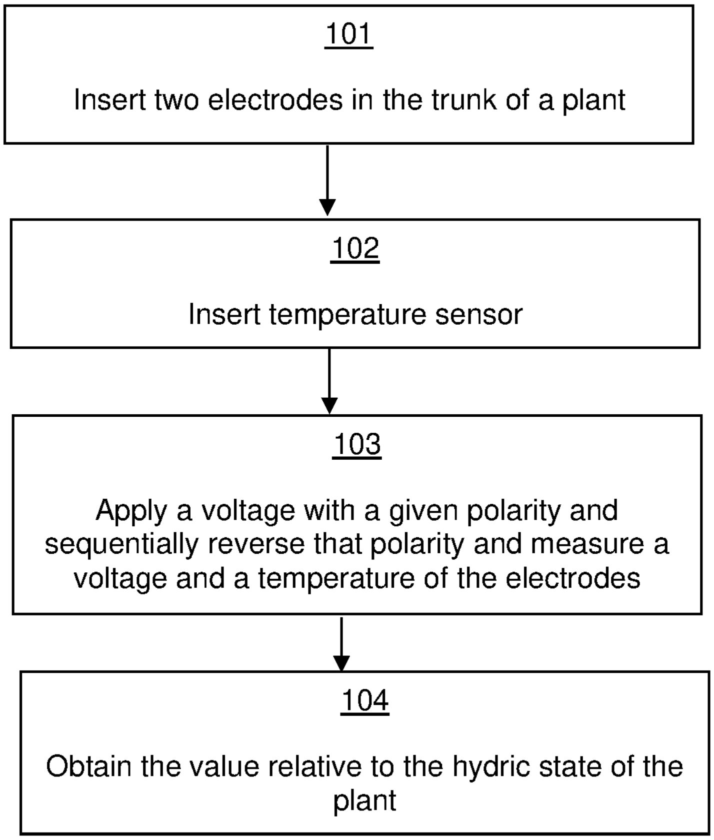
FIG. 2 is a flow diagram illustrating a method for measuring the hydric state of a plant, according to an embodiment of the present invention.

With reference now to FIG. 2, therein an embodiment of the proposed method is shown. According to this embodiment, at step 101, the two electrodes (12A, 12B) are inserted at a given depth into the trunk (T) of a plant to maintain galvanic contact with the plant. At step 102, the electrode temperature sensor (13) is inserted. In some examples, the electrode temperature sensor (13) is integrated within one of the electrodes (12A, 12B). Therefore, in these cases, steps 101 and 102 are performed at the same time.

Next, at step 103, the electronic unit (10), applies, during a first time interval, an electrical voltage at a given polarity on the electrodes (12A, 12B), inverts, sequentially, during a second time interval, said polarity, and measures, simultaneously, the temperature of the electrodes (and thus of the trunk (T) as the same are inserted therein) and some voltage values resulting from said application of electrical voltage at both polarities.

In some embodiments, the above step is performed until the electrical voltage in the area where the two electrodes (12A, 12B) are inserted is stable. For example, with a direct current injection, with a fixed applied voltage of, for example, 2.5 volts, during a time interval of 150 seconds, the measured and recorded value of voltage having passed through the electrodes and the plant, varies throughout the duration of the injection, going from values far from the voltage applied with the injection to values closer to this one; that is, they tend to resemble more the voltage at origin as the injection is extended in time. This fact responds to the phenomenon of polarization of electrically charged particles in the electric field formed between the two electrodes, with charged particles accumulating progressively. At the beginning the polarization is more accelerated and, progressively, it slows down. This slowdown in polarization and, therefore, in the variation of the measured voltage, is what is defined as signal stabilization. In other words, following the previous example, a variation of less than 0.1% of the voltage in 1% of the time, i.e. 0.0025 V in 1.5 s, being arbitrary in its conception, could be understood in the context of a stabilized signal.

In any case, and taking into account that the same degree of stabilization of the signal can occur at different times during the current injection, varying in the time in which it occurs, because the phenomenon of polarization depends, among other factors (e.g., electromagnetic radiation on the signal, temperature variation, etc.), on a greater or lesser presence of electric charges with free mobility in a fluid and, therefore, on the amount of fluid present in the area of the electric field (i.e., on the hydric state of the plant), alternatively, in other embodiments, it is preferable to set a fixed time, for instance, of approximately 150 seconds, to perform the voltage injection and measurement and to use a specific voltage data, for instance, at 149 seconds, to determine the conductance value to be used in the process of estimating the hydric state.

Following the explanation of FIG. 2, finally, at step 104, a processing unit determines the hydric state of the plant by implementing one or more algorithms on the measured data/parameters. Particularly, said one or more algorithms calculate the electrical conductance value, and with this calculated conductance value and the temperature of the electrodes the hydric state of the plant is finally inferred.

In some embodiments, and particularly if the electronic unit (10) includes said analog/digital converter (15), the measured voltage and temperature data/parameters are digitized prior to processing.

In some embodiments, at step 104, simultaneously with the other measurements, the temperature of the volume of air in contact with the temperature sensor (14), and/or the relative humidity of the volume of air in contact with the ambient humidity sensor, and/or the incident light radiation at the light radiation sensor can also be measured.

In a particular embodiment, from the resulting voltage values, a representative voltage value is selected, and from this value, the electrical conductance is calculated using the Wheatstone bridge equation:

$$\text{Conductancia} = \frac{V_{in} - V_{in}\left(1 + \frac{R_b}{R}\right)}{V_{in} \cdot R_b + V_m(R_b + R)} |$$

where: $V_{in}$ is the applied electrical voltage; $V_m$ is the measured voltage; and Rb and R are fixed and known resistances. Then the regression line is calculated, for example, for each day, between the series of electrical conductance and temperature measured in the trunk, for example, between the time period between 6 h and 14 h. Applying the formula of the regression line, the value of electrical conductance at the same temperature is obtained for each day.

To obtain a value relative to the hydric state of a plant, there are two ways to proceed, which are not mutually exclusive.

INDIVIDUAL EQUATION MODEL: In this case, a period of time is established in which the measurement system is installed in the plant and in which the branch water potential is also measured regularly. From a series of measurements of branch hydric potential and conductance at the same temperature, which show a linear relationship, the regression line between both parameters is obtained. Finally, the line is used to extrapolate the branch hydric potential corresponding to the conductance measurement at the same temperature measured with the measuring system, allowing to obtain, on a daily basis, a calculated value of the branch hydric potential.

GENERAL ECUATION MODEL: In this case, a single regression line is constructed for a species relating the conductance at the same temperature measured with the measurement system and the branch hydric potential. Given a set of plants in which the conductance at the same temperature and the branch water potential have been measured, a plant is selected whose conductance at the same temperature-branch hydric potential relationship is particularly good (base regression). For the rest of the plants, optimization is used to obtain the value (specific for each plant/equipment) that must be added or subtracted to all the points of the regression of that plant so that it fits better to the base regression. In this way, a single regression line is obtained between the branch hydric potential and the conductance at the same temperature of the whole set of plants (general line).

This general regression can be used in new installations of measurement systems on plants of the same species. For this purpose, a single measurement of the branch hydric potential is made at the time of installation of the equipment. From this measurement and the general line, the conductance value at the same temperature is obtained, which must be added or subtracted so that the measured value of the branch hydric potential is on the general line. This value (specific to each plant/equipment) will be used in the successive conductance measurements at the same temperature to calculate, with the desired periodicity, its branch hydric potential.

The scope of present invention is defined in the claims that follow.

The invention claimed is:

1. A system for evaluating the hydric state of a plant, comprising:

at least two electrodes (12A, 12B) separated a certain distance from each other, and adapted for its insertion, at a given depth, into the trunk of a plant to establish a galvanic contact with the plant;

at least one temperature sensor of the electrodes (13);

an electronic unit (10), operatively connected to the two electrodes (12A, 12B) and to the temperature sensor of the electrodes (13); and a processing unit including a memory and at least one processor, wherein the electronic unit (10) includes a voltage measurement module (21) configured to:

apply, during a first time interval, an electric voltage, with a given polarity, on the at least two electrodes (12A, 12B);

invert, sequentially, during a second time interval, said given polarity; and measure voltage values resulting from said application of electric voltage in both polarities carried out during said first and second time intervals;

wherein the temperature sensor of the electrodes (13) is configured to, simultaneously to said measurement, measure a temperature of the electrodes (12A, 12B); and wherein the at least one processor is configured to:

calculate an electrical conductance value from the applied electrical voltage and the resulting measured voltage values, and infer a value relative to the hydric state of the plant by processing the calculated conductance value and the measured electrode temperature.

2. The system of claim 1, wherein the voltage measurement module (21) comprises a Wheatstone bridge (22) adapted to allow the passage of electric current resulting from the electric voltage applied across it.

3. The system of claim 1, further comprising an analog-to-digital converter (15) adapted to, prior to processing, convert said resulting voltage values and the measured electrode temperature into equivalent digital signals.

4. The system of claim 1, wherein the electronic unit (10) further comprises an electrical power supply (18) including one or more batteries, one or more photovoltaic panels, or one or more thermoelectric generators.

5. The system of claim 1, further comprising an ambient temperature sensor (14).

6. The system of claim 1, further comprising one or more of the following elements: an ambient humidity sensor, a light radiation sensor, a geopositioning system, an internal operational error checking system and/or a real-time clock.

7. The system of claim 1, wherein the processing unit is remote to the electronic unit (10), wherein the processing unit and the electronic unit (10) each include a communications module.

8. The system of claim 1, wherein the processing unit is included in the electronic unit (10), wherein the electronic unit (10) further includes a communications module.

9. The system of claim 1, wherein the processing unit is remote to the electronic unit (10) and the electronic unit (10) includes a local processing unit (17), being both processing units connected to by means of a communications unit (19) of the electronic unit (10).

10. The system of claim 1, further comprising a fastening system (16) of the electronic unit (10) to the trunk of the plant.

11. The system of claim 1, wherein the electronic unit (10) includes a visualization interface.

12. A method for evaluating the hydric state of a plant, comprising:

a) inserting, at a given depth, at least two electrodes (12A, 12B) into a trunk of a plant, the two electrodes (12A, 12B) maintain a galvanic contact with the plant and are separated a certain distance from each other;

b) inserting at least one temperature sensor of the electrodes (13);

c) applying, by an electronic unit (10), during a first time interval, an electric voltage, with a given polarity, on the at least two electrodes (12A, 12B);

d) inverting, by the electronic unit (10), sequentially, during a second time interval, said given polarity;

e) measuring, by the electronic unit (10) using a voltage measurement module (and the temperature sensor of the electrodes (13), simultaneously, voltage values resulting from said application of electric voltage in both polarities carried out during said first and second time intervals and a temperature of the electrodes (12A, 12B);

f) calculating, by a processing unit, an electrical conductance value from the applied electrical voltage and the resulting measured voltage values, and g) calculating, by the processing unit, a value relative to the hydric state of the plant by processing the calculated conductance value and the measured electrode temperature.

13. The method of claim 12, wherein the voltage measurement module (21) comprises a Wheatstone bridge (22) that allows the passage of electric current resulting from the electric voltage applied across it.

14. The method of claim 12 or 13, wherein:

the first time interval and the second time interval have a fixed duration; or the application and inversion are performed until a stabilization of the electrical voltage in an area where the two electrodes (12A, 12B) are inserted.

15. The method of claim 12, further comprising, simultaneously to step e), a measurement of an ambient temperature near the plant and/or a measurement of an ambient humidity, light radiation, geolocation and/or a time stamp.

* * * * *